United States Patent [19]

Siebens et al.

[11] Patent Number: 5,505,198
[45] Date of Patent: Apr. 9, 1996

[54] UNIDIRECTIONAL AIRFLOW TRACHEOTOMY VALVE

[76] Inventors: Arthur A. Siebens, 617 W. 40th St., Baltimore, Md. 21211; Joseph French, 3-09 Blackburn Ct., Joppetatowne, Md. 21085

[21] Appl. No.: 281,612

[22] Filed: Jul. 28, 1994

[51] Int. Cl.⁶ .................................................. A61M 39/00
[52] U.S. Cl. ............................ 128/207.16; 128/911
[58] Field of Search ................... 128/207.16, 207.14, 128/207.15, 207.17, 207.20, 911, 912, DIG. 26; 137/533.11, 533.13

[56] References Cited

U.S. PATENT DOCUMENTS

| | | | |
|---|---|---|---|
| 3,066,674 | 12/1962 | Capra | 128/207.16 |
| 3,924,637 | 12/1975 | Swanson | 128/351 |
| 4,009,720 | 3/1977 | Crandall | 128/207.15 |
| 4,449,523 | 5/1984 | Szachowicz et al. | 128/200.26 |
| 4,459,984 | 7/1984 | Liegner | 128/207.15 |
| 4,573,460 | 3/1986 | Szachowicz et al. | 128/200.26 |
| 4,773,412 | 9/1988 | Blom et al. | 128/207.14 |
| 4,911,716 | 3/1990 | Blom et al. | 128/200.26 |
| 5,048,518 | 9/1991 | Eliachar et al. | 128/207.15 |
| 5,059,208 | 10/1991 | Coe et al. | 128/207.16 |
| 5,107,828 | 4/1992 | Koss et al. | 128/200.26 |

FOREIGN PATENT DOCUMENTS

| | | | |
|---|---|---|---|
| 3436777 | 4/1985 | Germany | 128/207.15 |
| 1217554 | 4/1968 | Sweden | 137/533.11 |

*Primary Examiner*—Edgar S. Burr
*Assistant Examiner*—V. Srivastava
*Attorney, Agent, or Firm*—Cushman Darby & Cushman

[57] ABSTRACT

A tracheotomy valve including a housing defining a chamber therein. The housing having a first opening located in a first plane at one end of the chamber and a second opening located in a vertical plane at another end of the chamber. The vertical plane and said first plane are angled with respect to one another such that a central axis of the first opening and a central axis of the second opening intersect and are angled with respect to one another. The tracheotomy valve also includes a displaceable element disposed in the chamber and movable therein. The displaceable element effects closing of the first opening when in a first position and moves from the first position during inspiration whereby the displaceable element is spaced apart from the first opening and air flows through the housing.

20 Claims, 6 Drawing Sheets

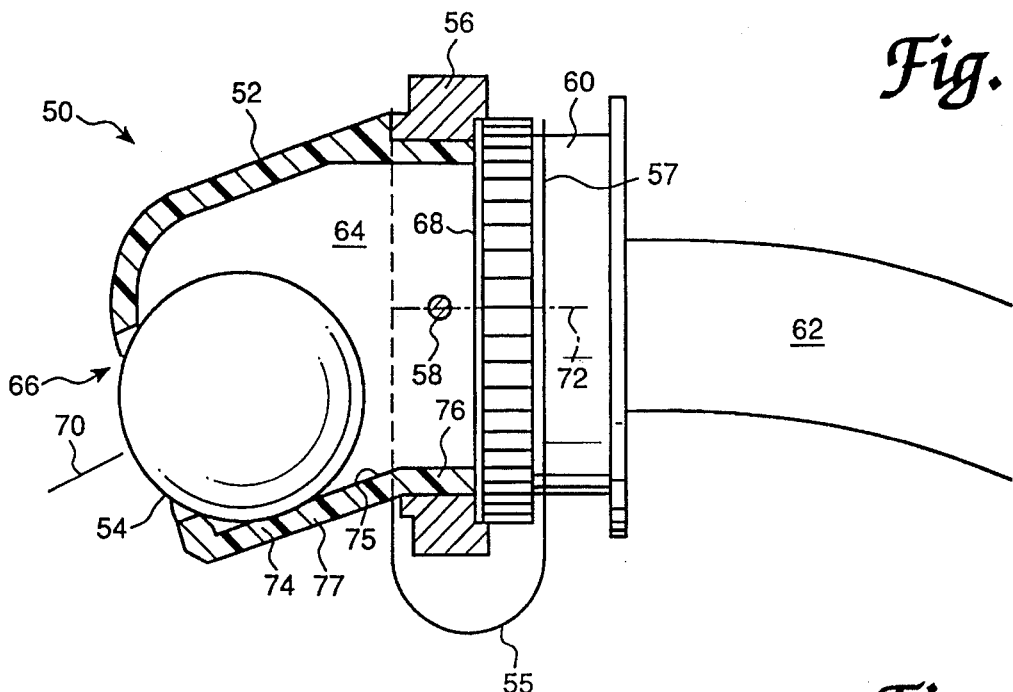
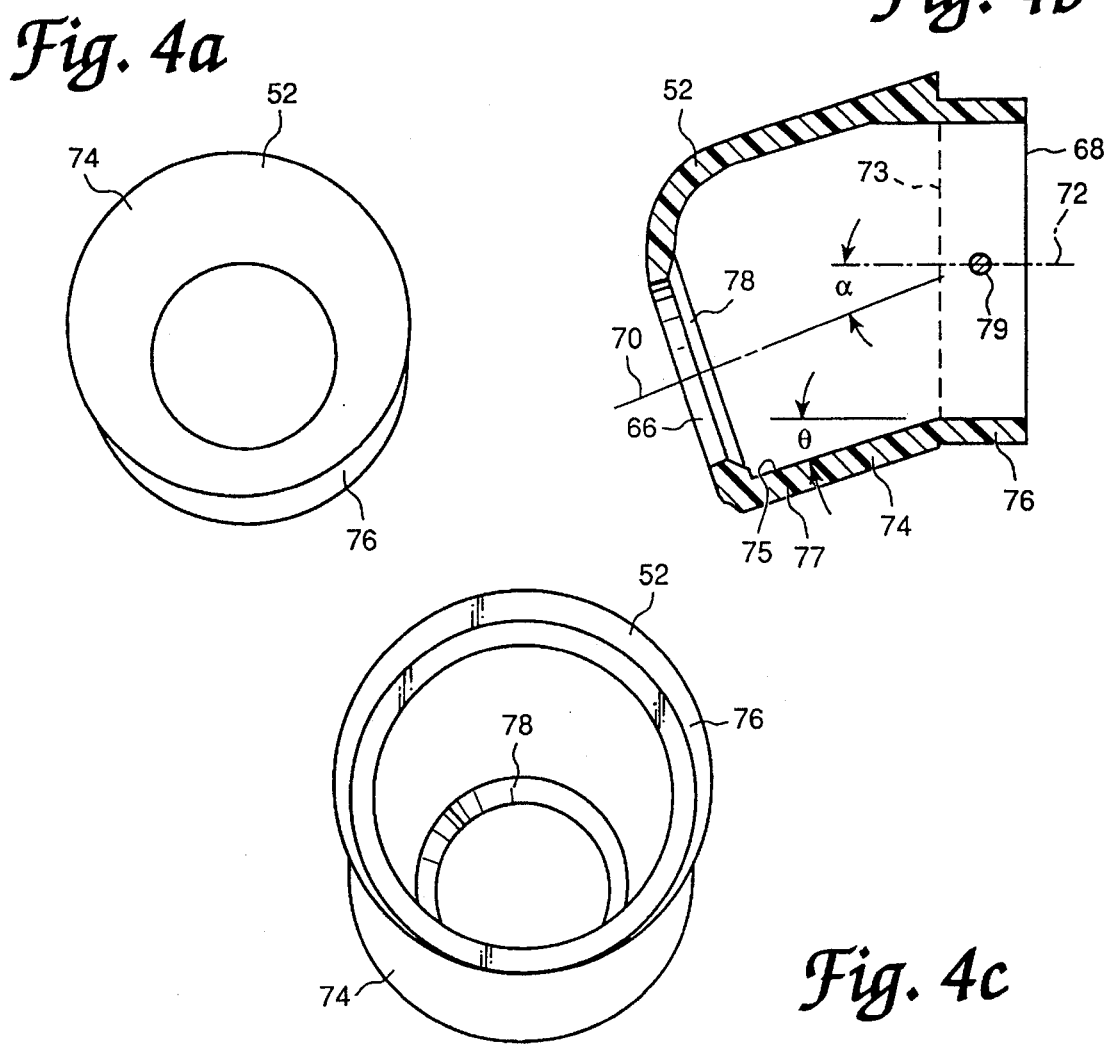

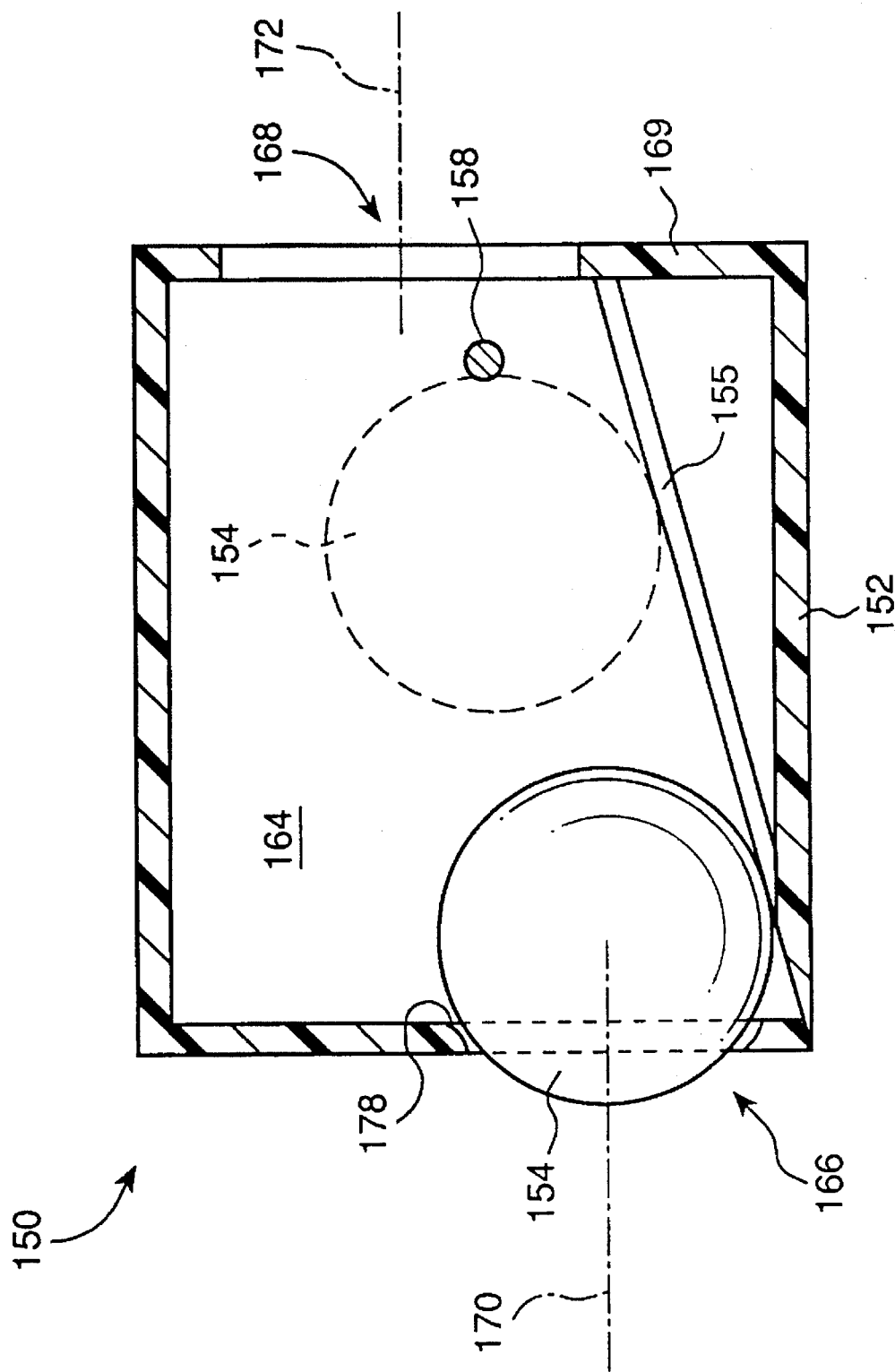

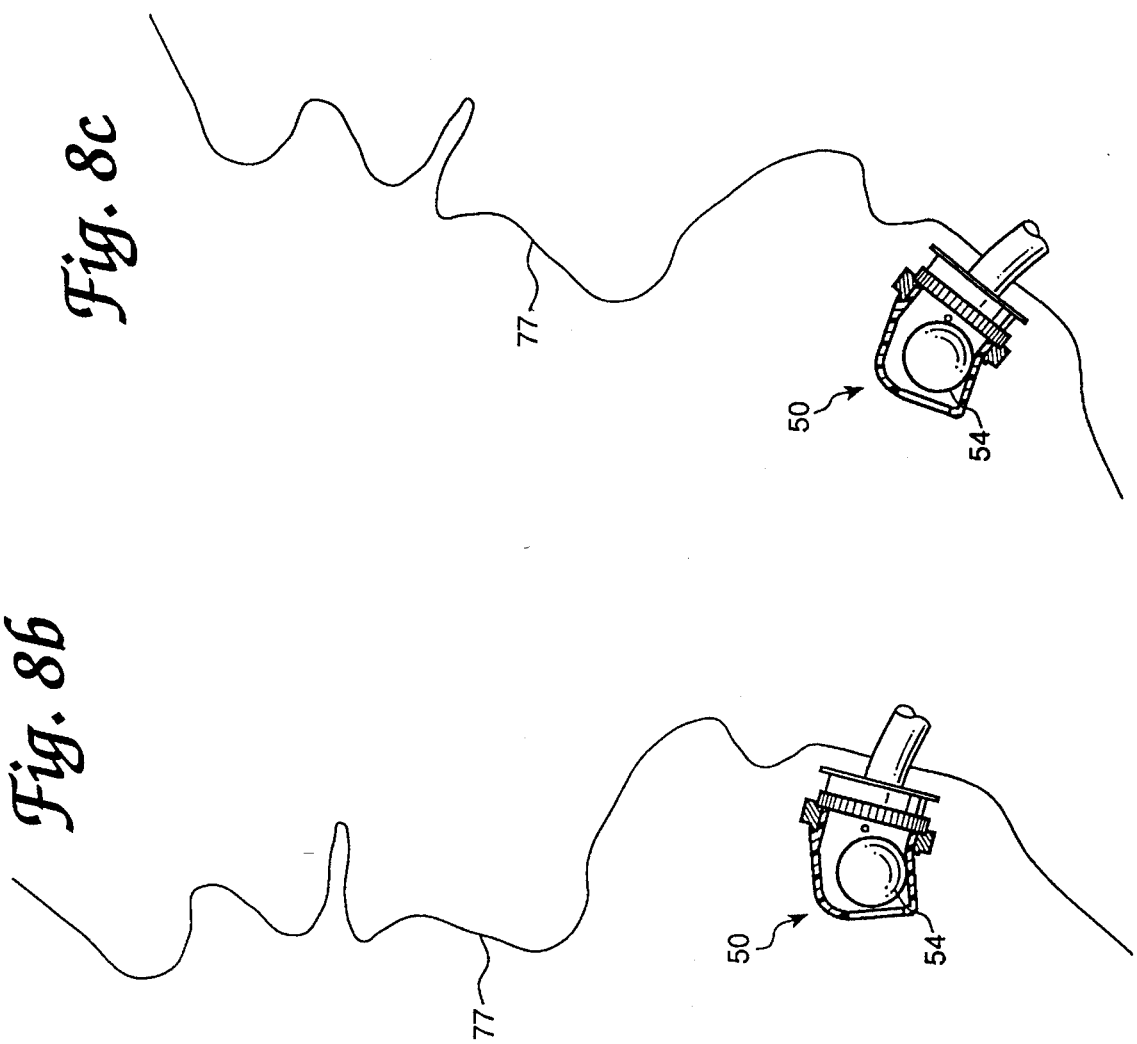
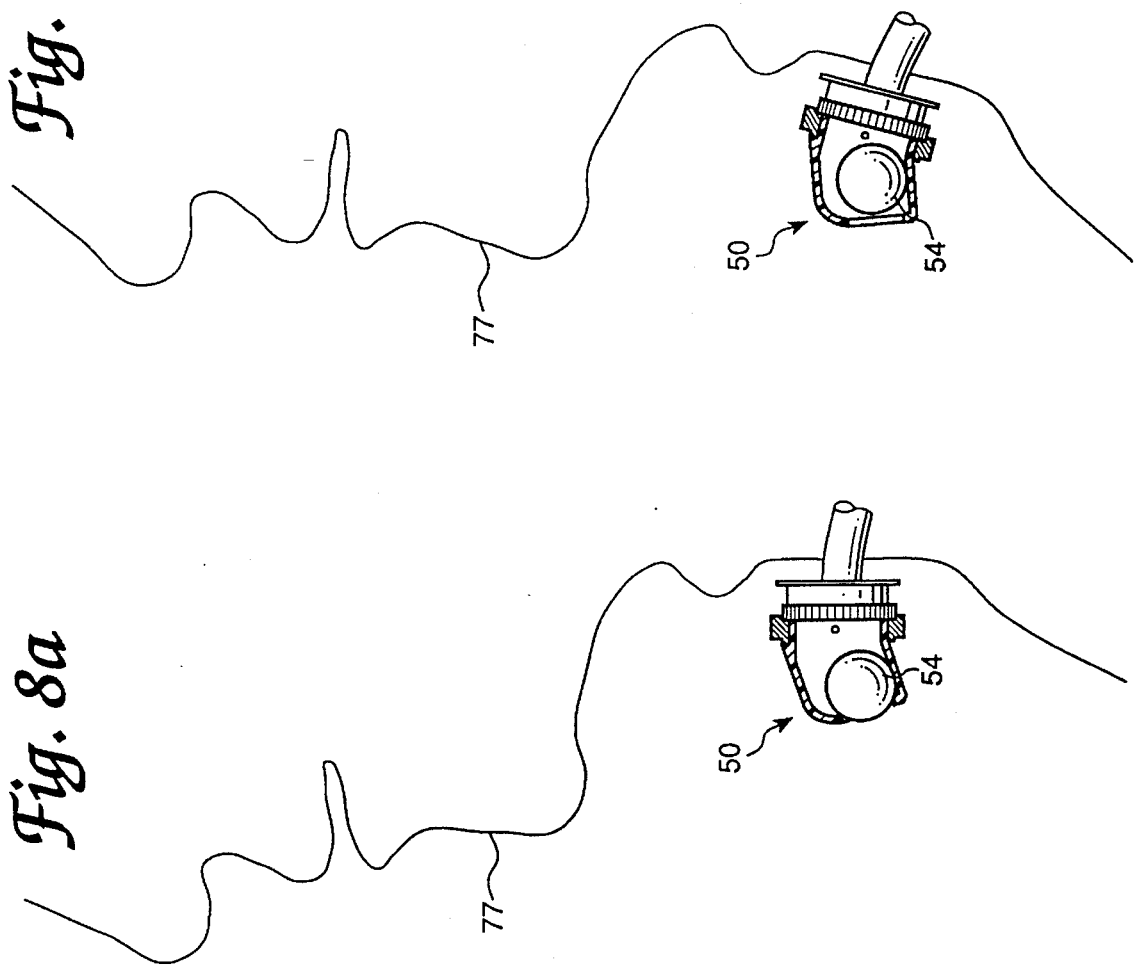

UNIDIRECTIONAL AIRFLOW TRACHEOTOMY VALVE

BACKGROUND OF THE INVENTION

1. Field of the Invention

The present invention pertains to a tracheotomy valve and, in particular, to an improved unidirectional tracheotomy valve that is easily actuated to close even by patients having relatively low tidal volumes and that operates reliably even if the patient is inclined from vertical over a range of angles.

2. Description of the Related Art

Unidirectional tracheotomy valves that are adapted to be mounted on the end of a cannula, which is inserted into the patient's trachea, are known, in general. Such valves allow air to flow through the cannula and into the lungs during inspiration and prevent air from flowing through the cannula during expiration. Thus, during expiration, air flows through the patient's upper airways, such as the subglottic trachea, larynx, pharynx, mouth, and nasal passages. As a result, tracheotomized individuals using a unidirectional tracheotomy valve are able to communicate orally and maintain clear upper airway passages by coughing or expelling air through the upper airway passages. Maintaining clear upper airway passages is important for safe oral alimentation as well as to prevent dystrophy of the muscles in the upper airways, for example.

FIGS. 1a–1c illustrate an original model of a unidirectional ball-valve assembly developed by the present inventors. In this device, a ball 20 is provided within a chamber 22 of housing 24, which includes a first opening 26 and a second opening 28 at either end of chamber 22. Housing 24 is attached to a cannula 30, which is inserted into the patient's trachea 32. During inspiration, as illustrated in FIG. 1b, air is drawn into chamber 22 through first opening 26, causing ball 20 to move to a second position proximate to second opening 28, being kept from occluding opening 28 by a thin wire stop (identified by numeral 27 in FIGS. 1a–1c). Thereafter, air flows through chamber 22 to the patient's lungs via cannula 30, as indicated by arrows 34. During expiration, as illustrated in FIG. 1c, air is forced into chamber 22 through second opening 28 causing ball 20 to move to a first position blocking first opening 26. As a result, air expelled from the patient's lungs does not pass through cannula 30, but instead is provided to the patient's upper airways as indicated by arrows 36. See FIG. 1c.

In order to block first opening 26 during expiration, ball 20 must traverse a distance d as illustrated in FIG. 1c. However, moving ball 20 distance d requires a relatively large expiration force. Consequently, some patients, especially those patients having relatively small tidal volumes, may not have a tidal volume and expiration force sufficient to block the first opening as air is expelled from the lungs. Furthermore, even in patients having larger tidal volumes, there is a fraction of a second delay after expiration is initiated before a sufficient expiration force is built up to move ball 20 into first opening 26 thereby enable phonation. This delay is sufficient to cause the leading syllable of a patient's utterance to be truncated or suppressed.

An improved unidirectional tracheotomy valve also developed by the present inventors is illustrated in FIGS. 2a–2c. This tracheotomy valve improves upon the conventional tracheotomy valve illustrated in FIGS. 1a–1c because less expiration force is required to close the valve and the delay before phonation commences is reduced to virtually zero, allowing speech to sound more natural. These improvements are achieved by eccentrically locating first opening 26a at the end of housing 24 such that a central axis 38 of first opening 26a is aligned with the center of ball 20. Because first opening 26a is eccentrically located on the end of housing 24, ball 20 does not need to be raised a distance d in order to block first opening 26a.

During inspiration, as illustrated in FIG. 2b, this tracheotomy valve functions in the same manner as the tracheotomy valve discussed above with respect to FIGS. 1a–1c. That is, air is drawn into chamber 22 causing ball 20 to move to a second position so that air flows through housing 24, cannula 30 and into the patient's lungs, as indicated by arrows 34. However, during expiration, which is illustrated in FIG. 2c, air is expelled from the lungs and enters chamber 22 causing ball 20 to roll directly into first opening 26a thereby blocking first opening 26a. When first opening 26a is blocked, air does not flow through housing 24 and cannula 30, but, instead, is provided to the patient's upper airways.

It has been found that the device illustrated in FIGS. 2a–2c functions adequately when the patient is in a vertical position. However, this device does not function reliably if the patient is reclined more than 20 degrees from vertical because the ball must move uphill against gravity. In addition, to function properly, housing 24 must be carefully positioned such that first opening 26a is located in the lower central portion of the end of the housing so that ball 20 rolls directly into the second opening.

SUMMARY OF THE INVENTION

It is, therefore, an object of the present invention to provide a unidirectional tracheotomy valve that is less sensitive to the position of the patient than the inventors' previous models so that the tracheotomy valve of the present invention operates reliably when the tracheotomized individual is inclined from vertical over a greater range of angles than previous models. It is a further object of the tracheotomy valve of the present invention to overcome the problems associated with the inventors' previous models of tracheotomy valves whereby the valve is not easily closed during expiration, even in patients with relatively large tidal volumes. Thus, patients with small tidal volumes can readily close the present tracheotomy valve.

In accordance with the principles of the present invention, the forgoing and other objects are achieved by providing a unidirectional tracheotomy valve that attaches to the exposed end of a cannula. The tracheotomy valve includes a housing defining a chamber therein. The housing has a first opening located at one end thereof and a second opening located at a second end thereof. The housing is attached to the cannula such that the second opening is located in a second plane which corresponds to the plane at the exposed end of the cannula when the valve is attached thereto. The first opening is located in a first plane that is inclined with respect to the second plane such that a central axis of the first opening and a central axis of the second opening intersect and are angled with respect to one another.

The tracheotomy valve includes a displaceable element disposed in the chamber and is movable therewithin. During a sufficiently large exhalation, the displaceable element effects a closing of the first opening when in a first position and is moved from the first position during inspiration whereby the displaceable element is spaced apart from the first opening so that air flows through the housing to the patient's lungs.

Other objects, features, and characteristics of the present invention, and the combination of parts and economies of manufacture will become more apparent upon consideration of the following description and the appended claims with reference to the accompanying drawings, all of which form a part of the specification, wherein like reference numerals designate corresponding parts in the various figures.

BRIEF DESCRIPTION OF THE DRAWINGS

FIG. 3 is a cross-sectional view of one embodiment of a unidirectional tracheotomy valve according to the principles of the present invention;

FIGS. 4a–4c are front, cross-sectional, and rear views, respectively, of the housing of the tracheotomy valve illustrated in FIG. 3;

FIG. 7 is a cross-sectional view of a second embodiment of a unidirectional tracheotomy valve according to the principles of the present invention;

FIGS. 8a–8c are side views, partially in section, of the tracheotomy valve illustrated in FIG. 3 attached to a cannula implanted in a patient.

DETAILED DESCRIPTION OF THE PRESENTLY PREFERRED EXEMPLARY EMBODIMENTS

Figure 1A:
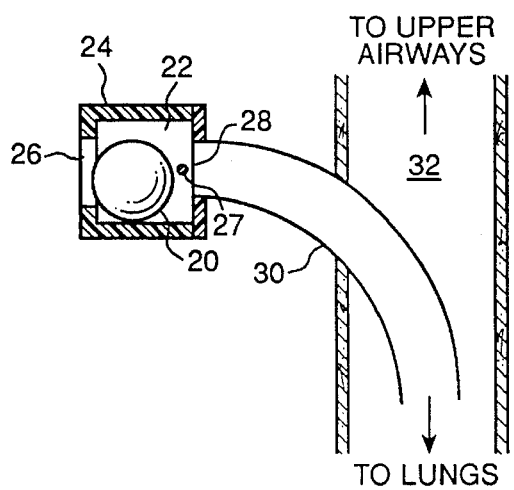
FIGS. 1a–1c are cross-sectional views of the inventors' original unidirectional tracheotomy valve.
Figure 2A:
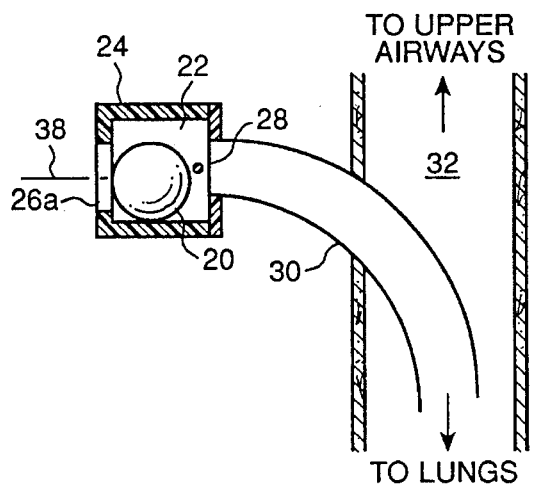
FIGS. 2a–2c are cross-sectional views of the inventors' improved unidirectional tracheotomy valve.
Figure 1B:
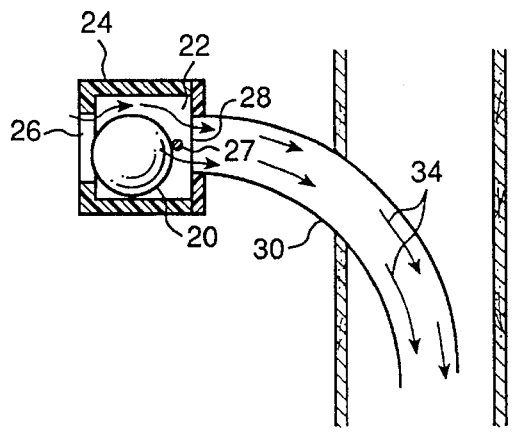
Figure 2B:
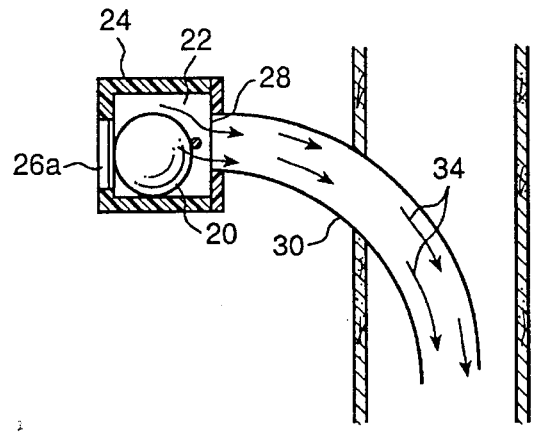
Figure 1C:
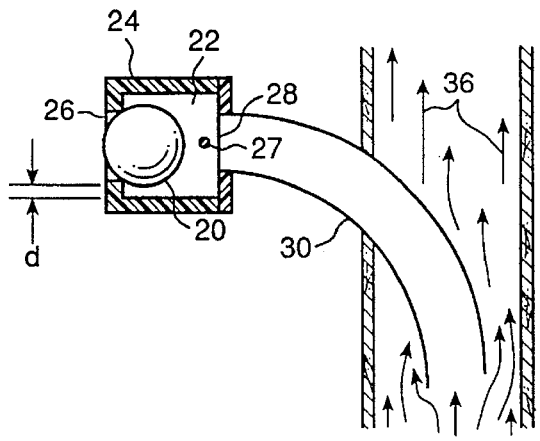
Figure 2C:
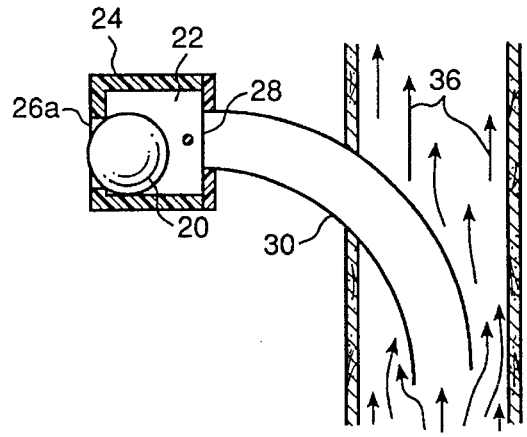
Figure 5A:
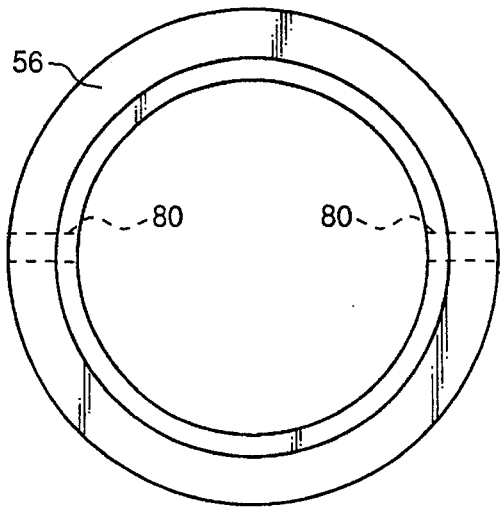
FIGS. 5a–5b are front and side views, respectively, of the flange associated with the housing of the tracheotomy valve illustrated in FIG. 3.
Figure 5B:
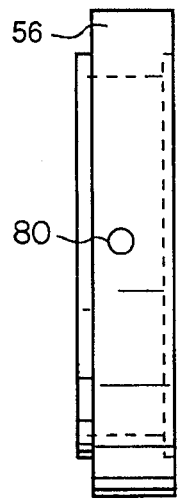

FIG. 3 illustrates one embodiment of a unidirectional tracheotomy valve, generally indicated at 50, according to the principles of the present invention, and FIGS. 4a–4c and 5a–5b illustrate the individual components comprising tracheotomy valve 50. Thus, in an exemplary embodiment of the present invention, tracheotomy valve 50 includes the following four major components: housing 52, ball 54, flange 56 and pin 58. In operation, tracheotomy valve 50 is attached to a end portion 60 of a cannula 62 and allows air to flow through housing 52 in only one direction. A detailed description of tracheotomy valve 50 is provided below.

Housing 52 defines a chamber 64 therein. A first opening 66 is eccentrically located at a first end of housing 52, and a second opening 68 is centrally located at a second end of housing 52. First and second openings 66 and 68 provide access to chamber 64 at the respective ends of housing 52. In this embodiment, second opening 68 is located in a second plane, which is a plane that corresponds to the plane defined at the end of the implanted cannula when the valve is attached thereto, and has a central axis 72. First opening 66 is located in another plane, which is inclined with respect to the second plane, and has a central axis 70. Central axis 70 and central axis 72 intersect one another at an angle α of between 0–30 degrees.

Figure 9B:
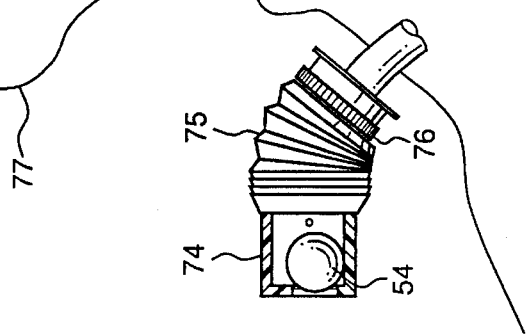
FIGS. 9a–9b are side views of a third embodiment of a unidirectional tracheotomy valve according to the principles of the present invention.
Figure 9A:
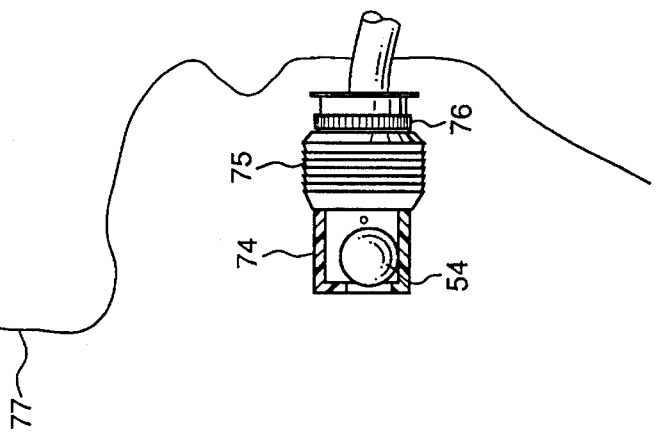

In a preferred embodiment of the present invention, housing 52 is generally tubular and includes a first tubular portion 74 extending from first opening 66 and a second tubular portion 76 extending from first tubular portion 74. First opening 66 is eccentrically located at the end of first tubular portion 74 such that central axis 70 of first opening 66 is aligned with the center of ball 54 when ball 54 is disposed on a surface 75 of wall 77. First tubular portion 74 is angled with respect to second tubular portion 76 by an angle Θ of between 0–30 degrees. In a preferred embodiment of the present invention, both angle Θ and angle α are 20 degrees. In an alternative embodiment of the present invention, the intersection of first tubular portion 74 and second tubular portion 76 is made from a flexible material 75 enabling first tubular portion 74 to be movable with respect to second tubular portion 76 so that angles Θ and α are adjustable over the range of 0–30 degrees See FIGS. 9a–9b. This embodiment of the present invention enables the path followed by ball 54 to be maintained in a horizontal plane even if patient 77 is reclined from vertical (FIG. 9b) so that gravity does not urge ball 54 in one direction or another, thereby minimizing the effect of gravity on ball 54.

In the embodiment illustrated in FIGS. 3 and 4b, first opening 66 is located in a plane perpendicular to a central axis of first tubular portion 74, and second opening 68 is located in a plane perpendicular to a central axis of second tubular portion 76. Because first tubular portion 74 is angled with respect to second tubular portion 76, first opening 66 and second opening 68 are located in planes that intersect one another, i.e., planes that are not parallel to one another. Second opening 68 is provided at the end of second tubular portion 76 such that a central axis of second tubular portion 76 and central axis 72 of second opening 68 are aligned with one another.

It is to be understood, however, that second tubular portion 76 can be substantially eliminated so that second opening is located in a plane defined, for example, by dashed line 73 in FIG. 4b.

Housing 52 is made from a light weight, nontoxic material suitable for use in medical devices. Such materials include slow burning, light weight, nontoxic plastics, metals, and/or carbon composite metal alloys. In a preferred embodiment of the present invention, housing 52 is made from a plastic material, for example, DERLIN, which is manufactured by E. I. DuPont Company.

Figure 6A:
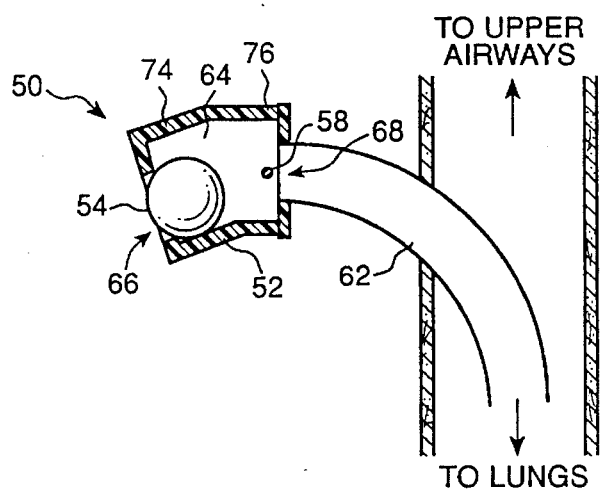
FIGS. 6a–6c are cross-sectional views showing the operation of the tracheotomy valve according to the principles of the present invention.

A displaceable element, which in the illustrated embodiments is a ball 54, is located in chamber 64 and is movable therein. In a first position, as illustrated in FIG. 6a, ball 54 effects closing of first opening 66 by entering first opening 66 and resting on a seat 78 (see FIGS. 4b–4c) provided around the interior periphery of first opening 66. It is to be understood, however, that ball 54 can effect closing of first opening 66 by other means when it is in the first position. For example, ball 54 can engage and displace a sealing element which in turn effects closing of first opening 66.

In the illustrated embodiments, ball 54 is maintained in the first position when the patient is in a vertical position due to the effect of gravity on the ball. More specifically, in the embodiment illustrated in FIG. 3, gravity causes ball 54 to roll along the inside surface 75 of wall 77 in housing 52 toward first opening 66 due to the angled relationship between the wall of housing 52 and vertical. Thus, ball 54 follows a path defined along the inside surface of the wall of housing 52.

It is to be understood, however, that other means, such as a spring member or elastic device can augment or effect the urging of ball 54 into the first position thereby effecting closing of first opening 66.

Ball 54 is moved from the first position by inspiration of the patient. The force of the air flowing to the lungs causes ball 54 to roll or otherwise shift toward the second opening along the interior surface of housing 52. Because ball 54 is spaced apart from the first position during inspiration, air flows through first opening 66 into chamber 64 and out chamber 64 through second opening 68 to the patient's lungs.

Ball 54 may be either solid or at least partially hollowed so that the weight of the ball is best suited to the patient's particular respiratory capacity. The greater the weight of ball 54, the more force is necessary to move the ball during expiration and inspiration. Juxtaposed against the desire to make ball 54 as light as possible is the need for ball 54 to be strong enough to withstand strong expiration forces, such as coughing, as well as repeated movement between the first and second positions. Suitable materials for ball 54 include materials that have low mass while maintaining sufficient a spherical shape against the patient's inspiration and expiration forces, such as nylon, polypropylene, or any other appropriate plastic, metal or composite material which is nontoxic and slow burning.

A blocking element, such as pin 58, prevents ball 54 from blocking second opening 68 when ball 54 is moved from the first position during inspiration. In a preferred embodiment of the present invention, pin 58 is provided such that it extends through a central axis of second tubular portion 76. However, it is to be understood that pin 58 can be provided at other positions within chamber 64. In addition to or in place of pin 58, other means, such as tabs extending toward the interior of chamber 64 from the surface of the walls of chamber 64, can be provided for stopping ball 54 so that it does not block second opening 68 when ball 54 it is moved away from the first position during inspiration. To provide guides for inserting pin 58 through housing 52, holes 79, shown in FIG. 4b, are provided on opposing sides of housing 52. In an exemplary embodiment of the present invention, pin 58 is a metal wire.

An attaching element, such as a flange 56, is provided around a periphery of second tubular portion 76 for attaching housing 52 to an end portion 60 of cannula 62. In a preferred embodiment of the present invention, tracheotomy valve 50 is removably attached to cannula 62 using a spring clip 55, as illustrated in FIG. 3. In an exemplary embodiment of the present invention, clip 55 is attached at one end to housing 52 and end portion 60 of cannula 62 is located between fingers at another end of clip 55. It is to be understood, however, that tracheotomy valve 50 can be attached to a cannula using any conventional means, such as a socket arrangement where a portion of the valve screws into the cannula or vice versa, and a snap-fit arrangement where a portion of the valve snaps into the cannula or vice versa. Other, more permanent, connections between cannula 62 and tracheotomy valve 50 are also contemplated by the present invention, such as bonding the valve to the cannula.

While tracheotomy valve 50 is illustrated in FIG. 3 as being attached to the end portion 60 of a Jackson-type cannula, it is to be understood that tracheotomy valve 50 can be attached to various types of cannulas, including other Jackson-type cannulas and Shiley cannulas, for example.

In a preferred embodiment of the present invention, flange 56 is attached to housing 52 using pin 58. Flange 56 is positioned on the end of housing 52 and includes holes 80 provided on opposing sides of flange 56. Holes 80 are aligned with holes 79 provided on housing 52. Pin 58 is then inserted through holes 79 and 80, thereby attaching flange 56 to housing 52 while also serving to stop ball 54 in the second position during inspiration, as was discussed above.

The operation of tracheotomy valve 50 is described below with reference to FIGS. 6a–6c and 8a–8c. When the patient is in a vertical position, as shown in FIGS. 6a–6c and 8a, and is not breathing in or out, the angled relationship between the first tubular portion 74 and the second opening 68, wherein the wall of chamber 64 slopes downward toward first opening 66, enables gravity to urge ball 54 into first opening 66 thereby effecting closing of first opening 66, as illustrated in FIG. 6a. Thus, when a patient using the tracheotomy valve of the present invention is in a vertical position, ball 54 is normally in the first position. Therefore, first opening 66 is normally closed.

Figure 6B:
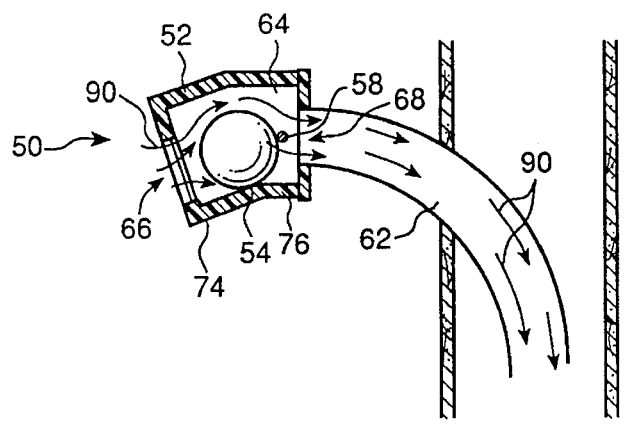

During inspiration, as illustrated in FIG. 6b, the force of the air drawn into chamber 64 causes ball 54 to move from the first position, where it blocks first opening 66 (see FIG. 6a) so that ball 54 is spaced apart from first opening 66 (see FIG. 6b). Pin 58 prevents ball 54 from blocking second opening 68. Air enters chamber 64 through first opening 66 and exits therefrom through second opening 68, as indicated by arrows 90. In this manner, air is provided to the lungs through tracheotomy valve 50.

Figure 6C:
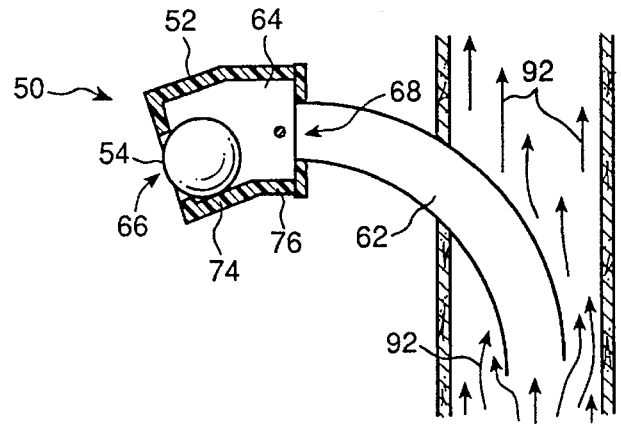

During expiration, as illustrated in FIG. 6c, the removal of the inspiratory force coupled with the downward slope of wall 77 (See FIG. 4b) of housing 52, causes ball 54 to move toward first opening 66, to the first position, thereby closing first opening 66. As a result, air expelled from the patient's lungs does not exit through cannula 62, but, instead, passes to and through the patient's upper airway, as indicated by arrows 92. Because the first tubular portion 74 is angled with respect to the vertical plane in which second opening 68 is located, gravity assists ball 54 in moving along a path defined along the interior surface of the wall of housing 52 to close first opening 66. Therefore, tracheotomy valve 50 operates reliably even if it is used by a patient having a relatively small tidal volume.

Furthermore, because first opening 66 is normally closed when the patient is in the vertical position, or inclined slightly, there is little or no delay before the patient can begin to phonate. Finally, the angled relationship between the first tubular portion 74 and the second tubular portion 76 (i.e., the vertical plane in which second opening 68 is located) allows tracheotomy valve 50 to function reliably even if the patient is inclined between 0–40 degrees from vertical.

As shown in FIG. 8b, if the patient is reclined from vertical, the path along which the ball rolls is moved closer to horizontal due to the angle between the tubular portions of the tracheotomy valve. As a result, the effect of gravity on ball 54, which causes ball 54 to move in one direction or another, is minimized. For example, if patient 77 is reclined by an angle equal to angle $\Theta$ (see FIGS. 4 and 8b), ball 54 lies in a substantially horizontal plane so that gravity does not urge ball 54 in one direction or another. If patient 77 is reclined as shown in FIG. 8c, i.e., at an angle greater than angle $\Theta$, the angle between the path followed by the ball and the plane defined at the end of the cannula to which the valve is attached reduces the degree of incline of the path followed by the ball, thereby minimizing the effect of gravity on ball 54. This is especially important because many tracheotomized individuals are also bedridden, and, therefore, must be inclined. The present invention allows these individual to phonate while they are inclined at a greater angle of inclination than the inventors' previous embodiments.

FIG. 7 illustrates another embodiment of the tracheotomy valve, generally indicated at 150, according to the principles of the present invention. In this embodiment, tracheotomy valve 150 includes a housing 152 defining a chamber 164 therein. A ball 154 is located in chamber 164 and is movable therein. A first opening 166 is located at one end of housing 152, and a second opening 168 is located at a second end 169 of housing 152. Second end 169 of housing 152 is attached to a cannula. In this embodiment, second opening 168 is located in a same plane as the plane defined by the end of the cannula and has a second central axis 172. First opening 166 is also located in this plane, and has a first central axis 170. First central axis 170 and second central axis 172 are parallel to one another and do not intersect.

As in the previous embodiment, first opening 166 is located such that central axis 170 is aligned with the center of ball 154 when ball 154 is in a first position, whereby ball 154 effects a closing of first opening 166. Moreover, in the illustrated embodiment, first opening 166 includes a seat 178 upon which ball 154 rests when in the first position.

Ball 154 moves within chamber 164 along a path within housing 152 by rolling over a guide element 155 that extends generally between first opening 166 and second opening 168. When ball 154 is in the first position, which is illustrated by solid lines, ball 154 effects closing of first opening 166. As in the previous embodiment, when the patient is in a vertical position, gravity urges ball 154 into the first position due to the inclined relationship of guide element 155 with respect to the plane in which the second opening 168 is located. As in the previous embodiment, the inclined relationship of guide element with respect to the plane in which the second opening is located minimizes the effect of gravity on ball 154 as the patient reclines from vertical. It is contemplated that the portion of housing 152 below guide element 155 may substantially reduced or eliminated to reduce the amount of material required to manufacture the tracheotomy valve. In addition, various shapes and configurations are possible for housing 152.

During inspiration, the force of the air causes ball 154 to move along guide element 155 such that ball 154 is spaced apart from first opening 166. This enables air to flow through housing 152 and into the patient's lungs. As in the previous embodiment, a blocking element, such as a pin 158, prevents ball 154 from blocking second opening 168 when ball 154 is moved from the first position during inspiration. The dashed lines illustrate ball 154 in a second position whereby pin 158 contacts ball 154 preventing it from entering second opening 168.

During expiration, gravity and the removal of the inspiratory force moves ball 154 into the first position, thereby effecting closing of first opening 166 so that air is expelled through the patient's upper airways rather than through the tracheotomy valve.

It, thus, can be appreciated that the objectives of this invention have been fully and effectively accomplished. It will be realized, however, that the foregoing preferred specific embodiment has been shown and described for the purpose of this invention and is subject to change without departure from such principles. Therefore, the present invention includes all modifications encompassed within the spirit and scope of the following claims.

What is claimed is:

1. A tracheotomy valve that attaches to an exposed end of a cannula implanted in a patient, comprising:

a housing defining a chamber therein, said housing having a first end and a second end, said first end including a first opening defined in a first plane, said first opening having a first central axis and providing access to said chamber at said first end of said housing and, said second end including a second opening defined in a second plane, said second opening having a second central axis and providing access to said chamber at said second end of said housing, said second end of said housing attaching to said exposed end of said cannula such that said second plane corresponds to a plane defined at said exposed end of said cannula to which said housing is attached, and said first plane being inclined with respect to said second plane such that said first central axis of said first opening and said second central axis of said second opening intersect and are angled with respect to one another; and a displaceable element disposed in said chamber and movable therein in a first direction generally along said first central axis of said first opening, said displaceable element being moved in substantially said first direction to a first position to effect a closing of said first opening during a sufficiently large exhalation and being moved from said first position during inspiration whereby said displaceable element is spaced from said first opening so that air can flow through said housing, said first central axis and said second central axis being positioned relative to one another so as to minimize movement of said displaceable element caused by the force of gravity acting on said displaceable member as the patient having the implanted cannula reclines from vertical while permitting said displaceable element to move freely into said first position during exhalation and out of said first position during inspiration.

2. A tracheotomy valve as defined in claim 1, wherein said displaceable element is a ball.

3. A tracheotomy valve as defined in claim 2, wherein said housing includes a seat provided around an interior periphery of said first opening for receiving said ball when in said first position thereby effecting closing of said first opening.

4. A tracheotomy valve as defined in claim 2, wherein said housing is made from a material selected from the group consisting of plastic and metal, and said ball is made from a material having a low mass and sufficient strength so as to maintain a spherical shape against forces acting on said ball.

5. A tracheotomy valve as defined in claim 1, further comprising a means for limiting displacement of said displaceable element toward said second opening when said displaceable element is moved from said first position during inspiration.

6. A tracheotomy valve as defined in claim 5, wherein said limiting means comprises a pin extending into said chamber and intersecting a path of travel of said displaceable element.

7. A tracheotomy valve as defined in claim 1, further comprising an attaching element that secures said second end of said housing to said exposed end of said cannula.

8. A tracheotomy valve as defined in claim 7, wherein said attaching element is a flange attached to said housing and selectively attachable to said cannula.

9. A tracheotomy valve as defined in claim 8, further comprising means for limiting displacement of said displaceable element toward said second opening when said displaceable element is moved from said first position during inspiration, said means for limiting displacement extending into said chamber and intersecting a path of travel of said displaceable element.

10. A tracheotomy valve as defined in claim 1, wherein said chamber includes a first tubular portion and a second tubular portion, said first tubular portion being inclined with respect to said second tubular portion, said first opening being located at an end of said first tubular portion remote from said second tubular portion and said second opening being located at an end of said second tubular portion.

11. A tracheotomy valve as defined in claim 10, wherein said first tubular portion includes a central axis and said second tubular portion includes a central axis, and wherein said first plane in which said first opening is defined is perpendicular to said central axis of said first tubular portion and said second plane in which said second opening is defined is perpendicular to said central axis of said second tubular portion.

12. A tracheotomy valve as defined in claim 11, wherein said first tubular portion and said second tubular portion are inclined up to 30 degrees relative to each other.

13. A tracheotomy valve as defined in claim 12, wherein said displaceable element is a ball and said first opening is circular.

14. A tracheotomy valve as defined in claim 13, further comprising a blocking element for preventing said ball from blocking said second opening when said ball is moved away from said first position.

15. A tracheotomy valve as defined in claim 14, further comprising a flange removably attached to said housing for attaching said housing to a cannula such that said second opening is adjacent to said cannula.

16. A tracheotomy valve as defined in claim 15, wherein said blocking element comprises a wire extending across said chamber, said wire also attaching said flange to said housing.

17. A tracheotomy valve that attaches to an exposed end of a cannula implanted in a patient, comprising:

a housing defining a chamber therein, said housing including a first opening to said chamber, said first opening being defined in a first plane at a first end of said housing, and a second opening to said chamber, said second opening being defined in a second plane at a second end of said housing, said second end of said housing being attached to said exposed end of said cannula such that said second plane and a plane defined by said exposed end of Said cannula are in a same plane which is not parallel to said first plane;

a ball disposed in said chamber and movable therein, said ball being moved to a first position at which said ball effects a closing of said first opening during a sufficiently large exhalation, if said ball is not already at said first position, and said ball being displaceable from said first position during inspiration whereby said ball is spaced apart from said first opening and air can flow through said housing; and means for urging said ball towards said first position to close said first opening when said patient is in a vertical position and for minimizing movement of said ball due to the force of gravity acting on said ball when said patient is in a reclined position while permitting said ball to move freely into said first position during exhalation and out of said first position during inspiration.

18. A tracheotomy valve as defined in claim 17, wherein an inclined path for said ball is defined between said first opening and said second opening and gravity urges said ball toward said first opening.

19. A tracheotomy valve as defined in claim 18, wherein said first opening includes a first central axis and said second opening includes a second central axis, and wherein first plane is inclined with respect to said second plane such that said first central axis of said first opening and said second central axis of said second opening intersect and are angled with respect to one another.

20. A tracheotomy valve that attaches to an exposed end of a cannula implanted in a patient, comprising:

a housing defining a chamber therein, said housing including a first tubular portion having a first end, a second end and a first opening to said chamber at said first end thereof, and a second tubular portion having first end, a second end and a second opening to said chamber at said second end thereof, said second end of said second tubular portion being attached to said exposed end of said cannula such that said second end of said second tubular portion and a plane defined by said exposed end of said cannula are in a same plane;

a flexible material attached to said second end of said first tubular portion and said first end of said second tubular portion, said flexible material enabling said first tubular portion to move relative to said second tubular portion;

a ball disposed in said chamber and movable therein, said ball being moved to a first position at which said ball effects a closing of said first opening during a sufficiently large exhalation, if said ball is not already at said first position, and said ball being displaceable from said first position during inspiration whereby said ball is spaced apart from said first opening and air can flow through said housing.

* * * * *